United States Patent [19]

Hsu et al.

[11] 4,299,976
[45] Nov. 10, 1981

[54] PREPARATION OF UNSATURATED DIESTER PRECURSOR FOR SEBACIC ACID

[75] Inventors: Chao-Yang Hsu, Media; Haven S. Kesling, Jr., Drexel Hill, both of Pa.

[73] Assignee: Atlantic Richfield Company, Los Angeles, Calif.

[21] Appl. No.: 80,354

[22] Filed: Sep. 28, 1979

[51] Int. Cl.³ .............................................. C07C 67/465
[52] U.S. Cl. .................................. 560/190; 252/431 C
[58] Field of Search ..................... 560/190; 252/431 C

[56] References Cited

U.S. PATENT DOCUMENTS 3,547,975  12/1970  Arad et al. .......................... 560/191
3,939,219  2/1976   Wilkinson ........................... 560/190

OTHER PUBLICATIONS

Zakharkin, L. I. et al. *Izv. Akad. Naut. SSSR, Ser. Khim.* (1976).
*Chemical Abstracts*, vol. 86 (1977) #16798c, p. 3638CS.
Araki, Takaaki et al. Japanese Pat. 75-16,763 (1975) See Chemical Abstracts vol. 83, 192521s (1975).
Bestmann, Hans J. et al. German 1,300,565 (1969) See Chemical Abstracts, vol 71, #91098t (1969).
Katagiri, Takao et al. Nippon Kagaku Kaishi (1977) No. 11 pp. 1742–1743, See Chemical Abstracts vol. 88 #50245w (1978).

*Primary Examiner*—Natalie Trousof
*Assistant Examiner*—L. Hendriksen
*Attorney, Agent, or Firm*—Delbert E. McCaslin

[57] ABSTRACT

A process for producing an unsaturated diester useful as a precursor for sebacic acid which comprises contacting, in a reaction inert medium, methyl penta-2,4-dienoate at a temperature of 30 to 150° C. under an inert atmosphere with a catalytic amount of a homogeneous palladium (II) complex of the formula

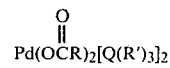

wherein Q is phosphorous or arsenic; R is alkyl, trichloroalkyl, tribromoalkyl or trifluoroalkyl having from 1 to 6 carbon atoms or aryl having 6 to 12 carbon atoms and R' is alkyl, aminoalkyl or alkoxy having 1 to 6 carbon atoms or aryl or aryloxy having 6 to 12 carbon atoms.

The foregoing precursor may subsequently be hydrogenated to dimethyl sebacate and sebacic acid may then be obtained by acid-catalyzed hydrolysis of dimethyl sebacate.

4 Claims, No Drawings

PREPARATION OF UNSATURATED DIESTER PRECURSOR FOR SEBACIC ACID

BACKGROUND OF THE INVENTION

Sebacic acid is used in making Nylon 6,10 and in alkyds. Alkyl sebacates such as dibutyl sebacate, dibenzyl sebacate and polypropylene sebacate are useful as plasticizers. Sebacic esters are excellent lubricants and are much superior to mineral oil products, particularly for use at extremely low temperatures. Certain metal sebacates can be used as fungicides, stabilizers or dryers. Sebacic anhydride may be used in epoxy resins.

There are several processes known in the art for the preparation of sebacic acid. One such process based on castor oil is currently commercialized. It involves caustic decomposition of ricinoleic acid at 245° C. to yield disodium sebacate and the hydrolysis of the disodium sebacate to afford sebacic acid. Several drawbacks are included in this process including high raw material coasts, the use of stoichiometric amounts of sodium hydroxide and sulfuric acid, low yield of sebacic acid (50–80%), and the production of a stoichiometric amount of 2-octanol by-product. All of these contribute to high production costs.

Another route to sebacic acid involves the oxidation of cyclodecane and produces the sebacic acid at essentially the same production costs as the castor oil process while avoiding the by-product problem.

A recent process involves a Kolbe type electrolytic dimerization of a methyl adipate salt. The main drawbacks of this process are the cost of adipic acid and the cost of energy utilized by the electrolytic process.

There is a wealth of literature relating to linear dimerization of conjugated olefins. Linear dimerization of 1,3-butadiene to octadiene or octatriene has been accomplished employing various transition metal catalysts including nickel, palladium, rhodium and platinum. Other olefins such as acrylic esters and acrylonitrile have also been dimerized to form a linear dimer employing transition metal catalysts.

The present invention is based on the discovery that sebacic acid can be prepared via the linear dimerization of methyl penta-2,4-dienoate followed by catalytic hydrogenation to dimethyl sebacate and conventional acid-catalyzed hydrolysis of the latter to sebacic acid.

BRIEF DESCRIPTION OF THE INVENTION

A process for producing an unsaturated diester useful as a precursor for sebacic acid which comprises contacting, in a reaction inert medium, methyl penta-2,4-dienoate at a temperature of 30° to 150° C. under an inert atmosphere with a catalytic amount of a homogeneous palladium (II) complex of the formula

wherein Q is phosphorous or arsenic; R is alkyl, trichloroalkyl, tribromoalkyl or trifluoroalkyl having from 1 to 6 carbon atoms or aryl having 6 to 12 carbon atoms and R' is alkyl, aminoalkyl or alkoxy having 1 to 6 carbon atoms or aryl or aryloxy having 6 to 12 carbon atoms.

The major reaction product in the aforesaid process is schematically shown as follows.

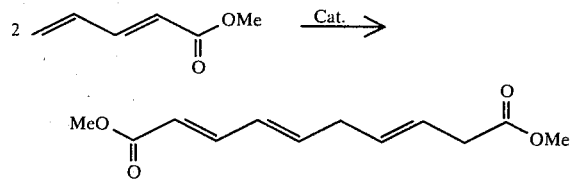

DETAILED DESCRIPTION OF THE INVENTION

In accordance with the present invention methyl penta-2,4-dienoate is reacted in an autoclave or any other reactor suitable for obtaining an inert atmosphere in contact with a catalytic amount of a homogeneous palladium (II) complex of the formula

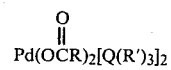

wherein Q is phosphorous or arsenic; R is alkyl, trichloroalkyl, tribromoalkyl or trifluoroalkyl having from 1 to 6 carbon atoms or aryl having 6 to 12 carbon atoms and R' is alkyl, aminoalkyl or alkoxy having 1 to 6 carbon atoms or aryl or aryloxy having 6 to 12 carbon atoms.

Generally, a catalytic amount of a homogeneous palladium (II) complex catalyst of the present invention ranges from about 0.1 to 5 mole% of the starting methyl penta-2,4-dienoate. Preferably, the amount of catalyst is between 0.5 and 2 mole % of said starting material.

The palladium (II) complex catalyst of the present invention is a homogeneous catalyst, i.e. it is soluble in the employed solvent medium. Typical examples of suitable solvents for the reaction inert medium of the present invention in which the catalyst is soluble include tetrahydrofuran, diethyl ether, dioxane, acetone, acetonitrile, methyl and ethyl acetate, chloroform, benzene, toluene, and dimethyl sulfoxide. The catalyst may be preformed or generated in situ. In the latter case, the molar ratio of

to $Q(R')_3$ preferably ranges from 1:0.5 to 1:3.

Preferred inert atmospheres for the purpose of the present invention include nitrogen and carbon dioxide at a pressure range of 15 to 750 psig.

The reaction of methyl penta-2,4-dienoate according to this invention should be conducted at a temperature of from 30° to 150° C. The preferred temperature is from 50° to 100° C.

The precursor containing reaction mixture of the present invention is preferably cooled to 0° C. to isolate the solid catalyst or the mixture can be subjected to fractional distillation so as to isolate the dimerization products and to recover the catalyst as a residue for possible recycle.

Hydrogenation of the precursor of the present invention can be carried out under a hydrogen pressure of from 1 to 50 atmospheres, preferably 1 to 10 atmospheres, and at a temperature of from 30° to 200° C., preferably from 100° to 125° C. The types of hydrogenation catalysts which may be employed in this hydrogenation have been extensively described in the prior art and any known hydrogenation catalyst, or mixture of catalysts, useful for the conversion of unsaturated esters to saturated esters may be used. Catalysts and the preparation thereof as described in U.S. Pat. Nos. 2,094,611, 2,201,235, and 3,374,184 and British Pat. Nos. 575,380, 1,151,567 and 1,181,137 may be used. In general heterogeneous catalysts comprising finely divided platinum, palladium, rhodium, ruthenium, cobalt and nickel which may be supported may be employed. Platinum oxides and palladium oxides, Raney nickel, platinum group metals on alumina or carbon may also be employed. Hydrogenation catalysts containing copper either in elemental form or combined with oxygen, as well as other hydrogenating metal oxides employed in conjunction with copper, supported or unsupported, may be used. Homogeneous hydrogenation catalysts may also be used, for example sodium carbonate tris(triphenylphosphine)rhodium chloride as described in British Pat. No. 1,181,137, hydrido tris(triphenylphosphine)ruthenium (II) chloride, tris(triphenylphosphine)ruthenium chloride and tripyridine rhodium (III) chloride. The amount of hydrogenation catalyst ranges from about 0.1 to 5 mole % of the starting methyl penta-2,4-dienoate which is dimerized.

After completion of the aforesaid hydrogenation, the hydrogenated methyl penta-2,4-dienoate and low boiling point reaction solvent medium can be removed from the reaction mixture by distillation under reduced pressure, e.g. $\leq 50°$ C. and 10 mm Hg. The methyl esters of the $C_{10}$-dicarboxylic acids can then be separated from the methyl ester of the $C_{15}$-tricarboxylic acid (trimer) and other minor-heavy by-products by distilling off the methyl esters of the $C_{10}$-dicarboxylic acids at reduced pressure, e.g. $\leq 135°$ C. under 0.5 mm Hg. The methyl esters of the $C_{10}$-dicarboxylic acids may then be subjected to stepwise crystallization using an appropriate solvent as illustrated by Example 9 hereinafter.

Conventional acid-catalyzed hydrolysis may be used for converting dimethyl sebacate to sebacic acid.

The following examples are for the purpose of illustrating the present invention and are not limiting to the scope thereof which is set forth in the claims.

EXAMPLE 1

Into a dry heavy wall glass reactor, there was introduced methyl penta-2,4-dienoate (25 mmole), diacetatebis(triphenylphosphine)palladium (II) (0.5 mmole), and toluene (20 ml). The reactor was sealed, and deoxygenated with a purge of nitrogen. While stirring, the reaction mixture was heated to 40° C. for 4 hours. After cooling the reaction mixture to 25° C. and separating the palladium complex catalyst, the reaction mixture was transferred to a Parr hydrogenation bottle. Palladium on carbon catalyst (5%, 1.0 g), and tetrahydrofuran (25 ml) was added into the reaction mixture. After the reaction system was purged with hydrogen, the reaction mixture was hydrogenated under 3 atm of hydrogen pressure until no further pressure drop was observed. The resulting hydrogenated reaction products were separated from the solid catalyst by filtration. The solvents were removed by distillation under reduced pressure. GLC analysis of the hydrogenated reaction mixture gives the following:

| Conversion (mole %) | 84.4 |
|---|---|
| Selectivity (mole %) | |
| linear[a] | 80.0 |
| branched[b] | 10.2 |
| cyclic[c] | 4.6 |
| trimer[d] | 5.2 |

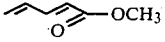

EXAMPLES 2–8

A series of runs was carried out employing different catalyst compositions under various reaction conditions. The same procedure as described in Example 1 was used except that the catalyst was generated in situ. The results are shown in Table 1.

TABLE 1

Dimerization of Methyl penta-2,4-dienoate Using Different Catalyst Compositions Under Various Reaction Conditions

| Example | 2 | 3 | 4 | 5 | 6 | 7 | 8 |
|---|---|---|---|---|---|---|---|
| Reagents, mmole | | | | | | | |
| Pd(OAC)$_2$ | 0.5 | 1.0 | 0.5 | 0.5 | 0.5 | 0.5 | 0.5 |
| Phosphine | PBu$_3$, 0.99 | PBu$_3$, 2.0 | P$\phi_3$, 0.96 | P$\phi_3$, 0.96 | P$\phi_3$, 0.99 | P$\phi_3$, 0.99 | PBu$_3$, 0.99 |
| 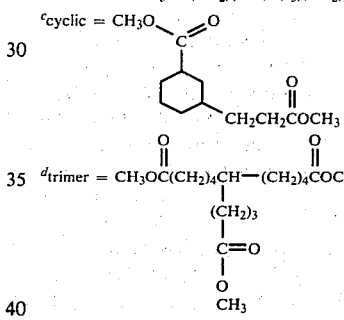 | 25 | 25 | 25 | 25 | 25 | 25 | 25 |
| Solvent (ml) | Toluene (20) | Methyl acetate (20) | Methyl acetate (20) | THF (20) | THF (20) | Acetonitrile (20) | Toluene (20) |
| Reaction Temperature (°C.) | 60 | 60 | 60 | 60 | 60 | 60 | 60 |
| Reaction Time (min) | 210 | 210 | 120 | 120 | 120 | 120 | 210 |
| Conversion (%) | 97.1 | 99.7 | 94.8 | 85.2 | 86.4 | 28.2 | 82.9 |
| Selectivity (%)* | | | | | | | |
| Linear | 74.0 | 74.5 | 67.9 | 73.0 | 73.8 | 69.9 | 72.3 |
| Branched | 8.9 | 7.7 | 15.1 | 14.8 | 13.9 | 7.5 | 9.2 |

TABLE 1-continued

Dimerization of Methyl penta-2,4-dienoate Using Different Catalyst Compositions Under Various Reaction Conditions

| Example | 2 | 3 | 4 | 5 | 6 | 7 | 8 |
|---|---|---|---|---|---|---|---|
| Cyclic | 1.9 | 1.6 | 3.7 | 1.1 | 1.1 | 1.2 | 2.7 |

*See Example 1

EXAMPLE 9

TABLE 2

Dimerization of Methyl penta-2,4-dienoate Using Different Catalyst Compositions Under Various Reaction Conditions

| Example | 10 | 11 | 12 | 13 | 14 | 15 | 16 |
|---|---|---|---|---|---|---|---|
| Reagents, mmole | | | | | | | |
| Pd | Pd(OAC)$_2$, 0.5 | Pd(OAC)$_2$, 0.5 | Pd(OCCF$_3$), 1 | Pd(OCCCl$_3$), 1 | Pd(OAC), 1 | Pd(OAC), 1 | Pd(OAC), 1 |
| Phosphine | (P—tol)$_3$P, 1 | (P—F$\phi$)$_3$P, 1 | P($\phi$)$_3$, 1 | P($\phi_3$), 1 | (Me$_2$N)$_3$P, 1 | ($\phi$O)$_3$P, 1 | ($\phi$)$_3$As, 1 |
| 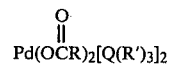—OCH$_3$ | 25 | 25 | 25 | 25 | 25 | 25 | 25 |
| Solvent (ml) | Toluene (20) | Toluene (20) | Toluene (20) | Toluene (20) | Toluene (20) | Toluene (20) | Toluene (20) |
| Temperature (°C.) | 60 | 60 | 60 | 60 | 60 | 60 | 60 |
| Time (min.) | 120 | 120 | 120 | 120 | 120 | 120 | 120 |
| Conversion (%) | >99 | 97.6 | 98.3 | 83.1 | 93.3 | 96.7 | 67.3 |
| Selectivity (%)* | | | | | | | |
| Linear | 61.8 | 66.7 | 77.5 | 61.5 | 79.2 | 73.1 | 59.2 |
| Branched | 11.9 | 9.5 | 6.1 | 15.8 | 7.8 | 6.7 | 19.3 |
| Cyclic | 3.9 | 4.0 | 3.4 | 5.1 | 4.2 | 4.1 | 6.7 |

*see Example 1

A methyl ester C$_{10}$-dicarboxylic acid mixture (24 g) containing dimethyl sebacate (81.5%), branched isomer (10.3%), cyclic isomer (1.1%), and other by-products (7.1%) was mixed with 24 ml of pentane at ambient temperature. The mixture was then cooled with an ice-water bath until temperature lowered to 0° C., at which point fine white crystals dropped out of solution. The upper liquid layer was then decanted. The crystals were then heated until a liquid was obtained, and 24 ml of pentane was added. After cooling to 0° C., while crystals again dropped out of the solution. The liquid pentane layer was decanted. The solids were then heated until completely liquefied, and the entrained pentane was stripped off by rotary evaporation. Gas chromatographic analysis of the isolated solid phase (17.7 g) revealed the following composition: dimethyl sebacate (99.0%), branched isomer (1.0%). The two decanted pentane phases were combined, after stripping off pentane, 6.3 g of methyl esters of C$_{10}$-dicarboxylic acids was obtained. The second recrystallization was then made by adding 6.3 ml of pentane, and the mixture was cooled to −5° C. An additional crop of solid (1.4 g) was separated. Gas chromatographic analysis of this crop revealed the following composition: dimethyl sebacate (92.4%), branched isomer (5.6%), cyclic isomer (0.6%), and others 1.4%. Thus, after two simple recrystallizations in pentane solvent, a 95.9% of dimethyl sebacate was recovered with a 98.4% purity.

EXAMPLES 10-16

A series of runs was carried out employing different catalyst compositions under various reaction conditions. The same procedure as described in Example 1 was used except that the catalyst was generated in situ. The results are shown in Table 2.

We claim:

1. A process for producing an unsaturated diester useful as a precursor for sebacic acid which consists essentially of contacting, in an inert reaction medium solvent selected from the group consisting of tetrahydrofuran, diethyl ether, dioxane, acetone, acetonitrile, methyl acetate, ethyl acetate, chloroform, benzene, toluene and dimethyl sulfoxide, methyl penta-2,4-dienoate at a temperature of 30° to 150° C. under an inert atmosphere with a catalytic amount of a homogeneous palladium (II) complex of the formula $$\text{Pd(OCR)}_2[\text{Q(R')}_3]_2$$

wherein Q is phosphorous or arsenic; R is alkyl, trichloroalkyl, tribromoalkyl or trifluoroalkyl having from 1 to 6 carbon atoms or aryl having 6 to 12 carbon atoms and R' is alkyl, aminoalkyl or alkoxy having 1 to 6 carbon atoms or aryl or aryloxy having 6 to 12 carbon atoms.

2. The process of claim 1 wherein said temperature is from 50° to 100° C.

3. The process of claim 1 wherein said inert atmosphere is nitrogen or carbon dioxide at a pressure of 15 to 750 psig.

4. The process of claim 1 wherein said catalyst is generated in situ by admixing Pd

(OCR)$_2$ with Q(R')$_3$ in a molar ratio of 0:0.5 to 1:3.

* * * * *

UNITED STATES PATENT OFFICE
CERTIFICATE OF CORRECTION

PATENT NO. : 4,299,976
DATED : November 10, 1981
INVENTOR(S) : Chao-Yang Hsu and Haven S. Kesling, Jr.

It is certified that error appears in the above-identified patent and that said Letters Patent are hereby corrected as shown below:

Column 6, Claim 4, Lines 59 -63 should read:

"....generated in situ by admixing $Pd(\overset{O}{\overset{\|}{O}CR})_2$ ....."

Signed and Sealed this

Ninth Day of February 1982

[SEAL]

Attest:

GERALD J. MOSSINGHOFF

*Attesting Officer*    *Commissioner of Patents and Trademarks*